(12) United States Patent
Kato

(10) Patent No.: US 8,786,863 B2
(45) Date of Patent: Jul. 22, 2014

(54) TRANSMITTED WAVEFRONT MEASURING METHOD, REFRACTIVE-INDEX DISTRIBUTION MEASURING METHOD, AND TRANSMITTED WAVEFRONT MEASURING APPARATUS THAT CALCULATE A FREQUENCY DISTRIBUTION AND OBTAIN A TRANSMITTED WAVEFRONT OF THE OBJECT BASED ON A PRIMARY FREQUENCY SPECTRUM IN THE FREQUENCY DISTRIBUTION

(75) Inventor: Seima Kato, Utsunomiya (JP)

(73) Assignee: Canon Kabushiki Kaisha (JP)

( * ) Notice: Subject to any disclaimer, the term of this patent is extended or adjusted under 35 U.S.C. 154(b) by 623 days.

(21) Appl. No.: 12/728,878

(22) Filed: Mar. 22, 2010

(65) Prior Publication Data
US 2010/0245842 A1 Sep. 30, 2010

(30) Foreign Application Priority Data
Mar. 25, 2009 (JP) .................................. 2009-074273

(51) Int. Cl.
*G01B 9/02* (2006.01)

(52) U.S. Cl.
USPC .......................................... 356/515; 356/520

(58) Field of Classification Search
USPC ......................................... 356/520, 511–515
See application file for complete search history.

(56) References Cited

U.S. PATENT DOCUMENTS

| | | | |
|---|---|---|---|
| 4,265,534 A | 5/1981 | Remijan | |
| 4,541,697 A | 9/1985 | Remijan | |
| 4,542,989 A | 9/1985 | Remijan | |
| 4,565,449 A | 1/1986 | Grego | |
| 4,744,654 A | 5/1988 | Jinno et al. | |
| 4,934,818 A | 6/1990 | Glantschnig et al. | |
| 5,151,752 A | 9/1992 | Oono et al. | |
| 5,309,214 A | 5/1994 | Hashimoto | |

(Continued)

FOREIGN PATENT DOCUMENTS

| | | |
|---|---|---|
| JP | 58-045526 A | 3/1983 |
| JP | 61-070436 A | 4/1986 |

(Continued)

OTHER PUBLICATIONS

Takeda, Mitsuo et al. "Lateral aberration measurements with a digital Talbot interferometer," Applied Optics, vol. 23, No. 11, Jun. 1, 1984, pp. 1760-1764.

(Continued)

*Primary Examiner* — Hwa Lee
(74) *Attorney, Agent, or Firm* — Rossi, Kimms & McDowell LLP

(57) ABSTRACT

A transmitted wavefront measuring method comprises the steps of emitting light 101 from a light source 100 onto an object to be measured 120 to receive interfering light transmitted through the object and a diffraction grating 130 on a light receiving portion 140 disposed at a predetermined distance from the diffraction grating to measure an intensity distribution of the interfering light T10, performing a Fourier transform of the intensity distribution to calculate a frequency distribution T20, and obtaining a transmitted wavefront of the object based on a primary frequency spectrum in the frequency distribution T30 to T90. The step of obtaining the transmitted wavefront comprises the steps of performing an inverse Fourier transform of the primary frequency spectrum with reference to a grating frequency of the diffraction grating to calculate a complex amplitude of the interfering light T60, and obtaining the transmitted wavefront based on the complex amplitude T90.

5 Claims, 5 Drawing Sheets

(56) References Cited

U.S. PATENT DOCUMENTS

| | | |
|---|---|---|
| 5,526,118 A | 6/1996 | Miyagawa et al. |
| 6,765,661 B2 | 7/2004 | Biel et al. |
| 7,388,676 B2 | 6/2008 | Sawada |
| 2006/0159332 A1 | 7/2006 | Sawada |
| 2007/0109555 A1 | 5/2007 | Gustafsson et al. |
| 2009/0109401 A1 | 4/2009 | Van Heugten |
| 2009/0147241 A1 | 6/2009 | Shlezinger et al. |
| 2010/0165355 A1 | 7/2010 | Kato |
| 2011/0134438 A1 | 6/2011 | Kato |
| 2011/0292379 A1 | 12/2011 | Kato |
| 2012/0139136 A1 | 6/2012 | Kato |
| 2012/0241989 A1 | 9/2012 | Sugimoto |

FOREIGN PATENT DOCUMENTS

| | | |
|---|---|---|
| JP | 1-035282 B2 | 7/1989 |
| JP | 1316627 A | 12/1989 |
| JP | 02-008726 A | 1/1990 |
| JP | 3-128411 A | 5/1991 |
| JP | 03-225259 A | 10/1991 |
| JP | 08-014852 A | 1/1996 |
| JP | 08-304229 A | 11/1996 |
| JP | 11-044641 A | 2/1999 |
| JP | 2005-106835 A | 4/2005 |
| JP | 2005-201724 A | 7/2005 |
| JP | 2006-200999 A | 8/2006 |
| JP | 2010-151578 A | 7/2010 |

OTHER PUBLICATIONS

Takeda, Mitsuo et al. "Fourier-transform method of fringe-pattern analysis for computer-based topography and interferometry," Optical Society of America, Vo. 72, No. 1, Jan. 1982, pp. 156-160.

Ranjbar, et al., "Nondestructive Measurement of Refractive Index Profile of Optical Fiber Preforms Using Moire Technique and Phase Shift Method", Optical Communication, vol. 6025, 605250, 2006.

ISR issued Aug. 30, 2011 for PCT/JP2011/062041.

TRANSMITTED WAVEFRONT MEASURING METHOD, REFRACTIVE-INDEX DISTRIBUTION MEASURING METHOD, AND TRANSMITTED WAVEFRONT MEASURING APPARATUS THAT CALCULATE A FREQUENCY DISTRIBUTION AND OBTAIN A TRANSMITTED WAVEFRONT OF THE OBJECT BASED ON A PRIMARY FREQUENCY SPECTRUM IN THE FREQUENCY DISTRIBUTION

BACKGROUND OF THE INVENTION

1. Field of the Invention

The present invention relates to a transmitted wavefront measuring method using a Talbot interferometer.

2. Description of the Related Art

Previously, as one of methods of measuring a transmitted wavefront of a test optical system (a test object) having a large aberration, a measuring method using a Talbot interferometer as disclosed in APPLIED OPTICS/Vol. 23, No. 11/1984, pp 1760-1764 (reference 1) is known. According to reference 1, a Talbot condition (a condition where an interference pattern appears) is represented as the following expression (1) using a distance $Z_t$ between a diffraction grating and an image pickup element and a distance $Z_0$ between the diffraction grating and an image point of the test optical system.

$$\left(\frac{Z_0 Z_t}{Z_0 - Z_t}\right) \cdot \left(\frac{\lambda}{2d^2}\right) = N \quad (1)$$

In the expression (1), d is a pitch (a period) of a diffraction grating, $\lambda$ is a wavelength of a light source, and N is an integer. A frequency $f_0$ of an interference pattern in this case is represented as the following expression (2).

$$f_0 = \frac{Z_0}{(Z_0 - Z_t)d} \quad (2)$$

When the transmitted wavefront is restored using the interference pattern, an FFT method (a Fast Fourier Transform method) is commonly used. J. Opt. Soc. Am./Vol. 72, No. 1/1982, pp 156-160 (reference 2) discloses a technology for moving a first spectrum on a spatial frequency of the interference pattern by a spatial carrier frequency to restore the transmitted wavefront of the test optical system with regard to the FFT method. Reference 1 also discloses a case where a transmitted wavefront of a test optical system can be restored by analyzing the frequency $f_0$ defined by the expression (2) as a spatial carrier frequency in reference 2. This uses a phenomenon where an aberration of the test optical system causes a spectral broadening when the interference pattern is represented on the spatial frequency.

Commonly, position information of an interference spectrum is a tilt component of a phase distribution. In a shearing interferometer such as a Talbot interferometer, the tilt component of the phase distribution becomes a focus component of a transmitted wavefront shape. Therefore, there is also a method of ignoring the position information of the interference spectrum to obtain a transmitted wavefront where the focus component has been removed.

In the method of restoring the transmitted wavefront as described above, in order to measure the transmitted wavefront including the focus component, it is necessary to exactly recognize the distance $Z_t$ between the diffraction grating and the image pickup element and the distance $Z_0$ between the diffraction grating and the image point of the test optical system. However, when the aberration of the test optical system is large, it is difficult to exactly determine the spatial carrier frequency $f_0$ that is a reference in obtaining the focus component because the test optical system does not have one image point. Even if these distances $Z_t$ and $Z_0$ can be exactly determined, it is difficult to exactly dispose an optical element of a measuring system at a designed position. Thus, in a conventional technology, when the test optical system with a large aberration is measured by using the Talbot interferometer, the focus component cannot be measured with a high degree of accuracy.

BRIEF SUMMARY OF THE INVENTION

The present invention provides a transmitted wavefront measuring method capable of measuring a transmitted wavefront of a test object including a focus component with high accuracy.

A transmitted wavefront measuring method as one aspect of the present invention comprises the steps of emitting light from a light source onto an object to be measured to receive interfering light transmitted through the object to be measured and a diffraction grating on a light receiving portion disposed at a predetermined distance from the diffraction grating to measure an intensity distribution of the interfering light, performing a Fourier transform of the intensity distribution of the interfering light to calculate a frequency distribution, and obtaining a transmitted wavefront of the object to be measured based on a primary frequency spectrum in the frequency distribution. The step of obtaining the transmitted wavefront comprises the steps of performing an inverse Fourier transform of the primary frequency spectrum with reference to a grating frequency of the diffraction grating to calculate a complex amplitude of the interfering light, and obtaining the transmitted wavefront of the object to be measured based on the complex amplitude of the interfering light.

A refractive-index distribution measuring method as another aspect of the present invention comprises the steps of measuring a first transmitted wavefront of the object to be measured in a first medium whose refractive index is different from that of the object to be measured, measuring a second transmitted wavefront of the object to be measured in a second medium whose refractive index is different from the object to be measured and the first medium, and calculating a refractive-index distribution of the object to be measured based on the first transmitted wavefront and the second transmitted wavefront. The steps of measuring the first transmitted wavefront and the second transmitted wavefront are performed by the transmitted wavefront measuring method.

A method of manufacturing an optical element as another aspect of the present invention comprises a step of fabricating an optical element based on a transmitted wavefront of the optical element measured by the transmitted wavefront measuring method or the refractive-index distribution measuring method.

A transmitted wavefront measuring apparatus as another aspect of the present invention comprises a light source configured to emit light onto an object to be measured, a diffraction grating configured so that the light emitted from the light source enters the diffraction grating, a light receiving portion configured to be disposed at a predetermined distance from the diffraction grating and to receive an intensity distribution of an interfering light transmitted through the object to be measured and the diffraction grating, a frequency distribution calculator configured to perform a Fourier transform of the intensity distribution of the interfering light to calculate a frequency distribution, and a transmitted wavefront calculator configured to obtain a transmitted wavefront of the object to be measured based on a primary frequency spectrum in the frequency distribution. The transmitted wavefront calculator performs an inverse Fourier transform of the primary frequency spectrum with reference to a grating frequency of the diffraction grating to calculate a complex amplitude of the interfering light to obtain the transmitted wavefront of the object to be measured based on the complex amplitude of the interfering light.

Further features and aspects of the present invention will become apparent from the following description of exemplary embodiments with reference to the attached drawings.

DETAILED DESCRIPTION OF THE PREFERRED EMBODIMENTS

Figure 1:
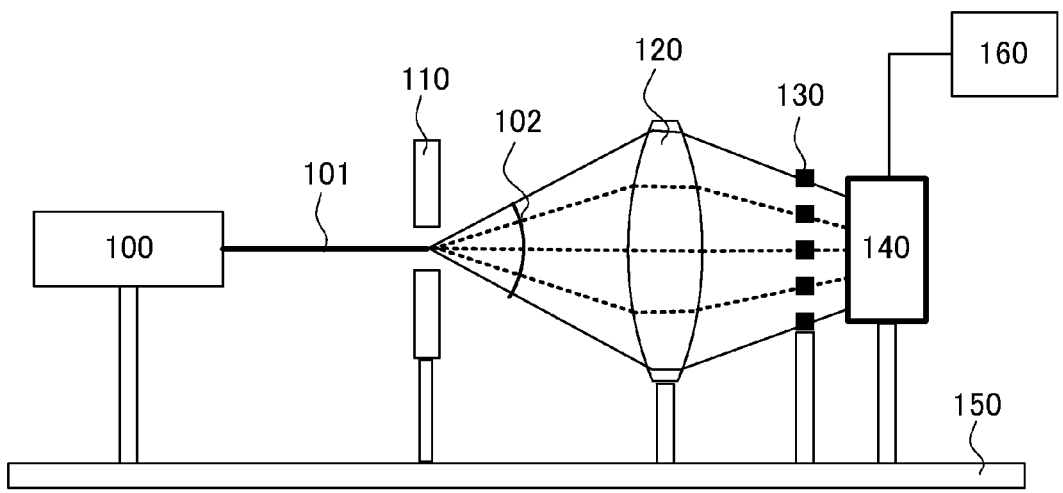
FIG. 1 is a schematic configuration diagram of a transmitted wavefront measuring apparatus in accordance with a first embodiment (Embodiment 1) of the present invention.

Exemplary embodiments of the present invention will be described below with reference to the accompanied drawings. In each of the drawings, the same elements will be denoted by the same reference numerals and the duplicate descriptions thereof will be omitted.

Embodiment 1

First, a transmitted wavefront measuring apparatus and a transmitted wavefront measuring method in Embodiment 1 of the present invention will be described. The measuring apparatus and the measuring method of the present embodiment are capable of measuring a transmitted wavefront of a single lens or a unit lens in a product with a large aberration (a test object) including a focus component with a high degree of accuracy. In the present embodiment, the transmitted wavefront includes a wavefront reflected off of a mirror or the like in addition to a wavefront transmitted through a lens or an optical system.

FIG. 1 is a schematic configuration diagram of the transmitted wavefront measuring apparatus in the present embodiment. In FIG. 1, reference numeral 100 denotes a laser light source for emitting light onto a test object 120 (an object to be measured). A laser light 101 emitted from the laser light source 100 passes through a pinhole 110 and is diffracted by the pinhole 110. A laser light 102 diffracted by the pinhole 110 passes through the test object 120 where the pinhole 110 is an object surface. A diameter φ of the pinhole 110 is so small that the laser light 102 (diffracted light) is considered as a substantially ideal spherical surface. The diameter φ of the pinhole 110 is designed so as to satisfy the following expression (3) using an opening NAO at an object side and a wavelength λ of the laser light source 100.

$$\varphi \approx \frac{\lambda}{NAO} \quad (3)$$

For example, when the wavelength λ is 600 nm and the opening NAO at the object side is around 0.3, the diameter φ of the pinhole 110 is around 2 μm. The laser light 102 passing through the test object 120 passes through a diffraction grating 130 (a two-dimensional orthogonal diffraction grating) to be received by a CCD 140 (a light receiving portion). The laser light 102 received by the CCD 140 is measured by a controller 160 and each kind of process is performed. When a distance between the diffraction grating 130 and the CCD 140 is defined as $Z_t$ and a distance between the diffraction grating 130 and a collecting point of the test object (not shown) is defined as $Z_0$, a spurious resolution of the diffraction grating 130 can be obtained as an interference pattern on the CCD 140 in a case where these distance $Z_t$ and $Z_0$ satisfy the condition represented by the above expression (1). In the present embodiment, the laser light source 100, the pinhole 110, the test object 120, the diffraction grating 130, and the CCD 140 are arranged on a rail 150 disposed in parallel to an optical axis of the test object 120, and are configured so as to be movable on the rail 150.

Figure 2:
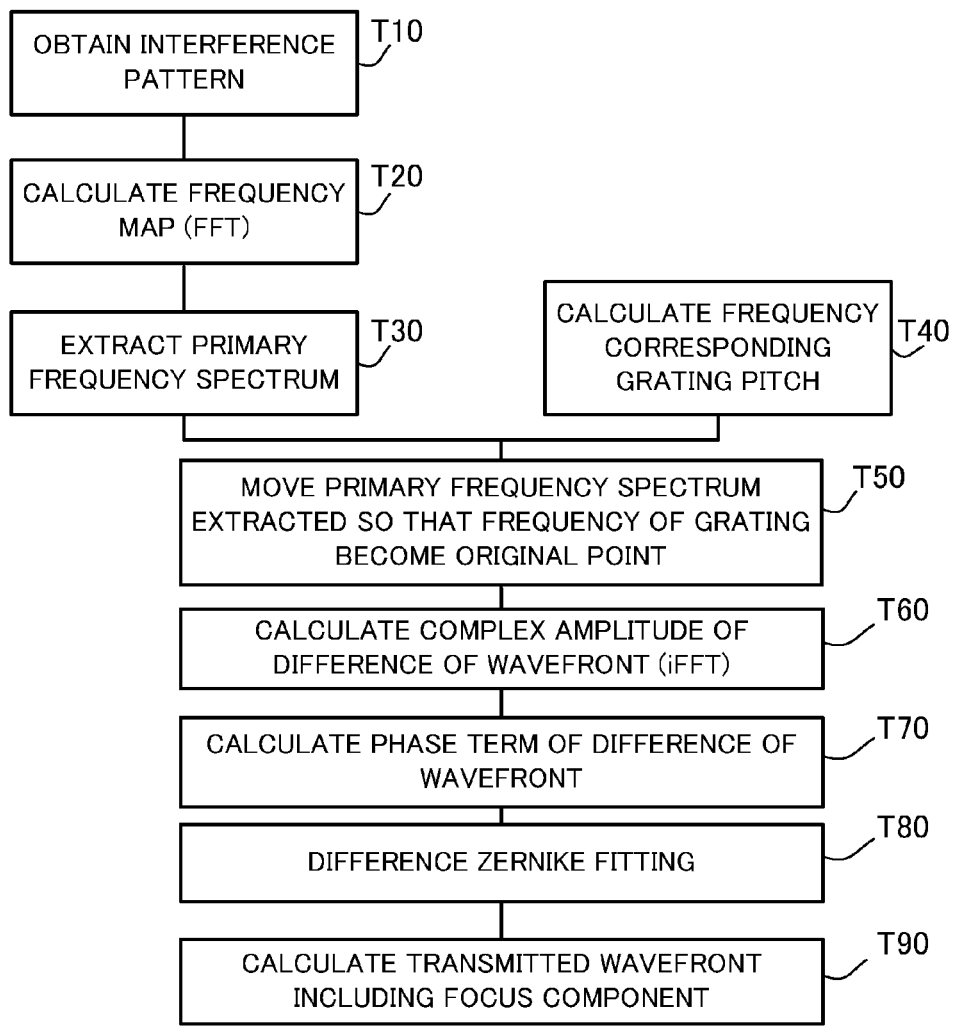
FIG. 2 is a flow diagram of a transmitted wavefront measuring method utilizing the apparatus of FIG. 1 (Embodiment 1).
Figure 3:
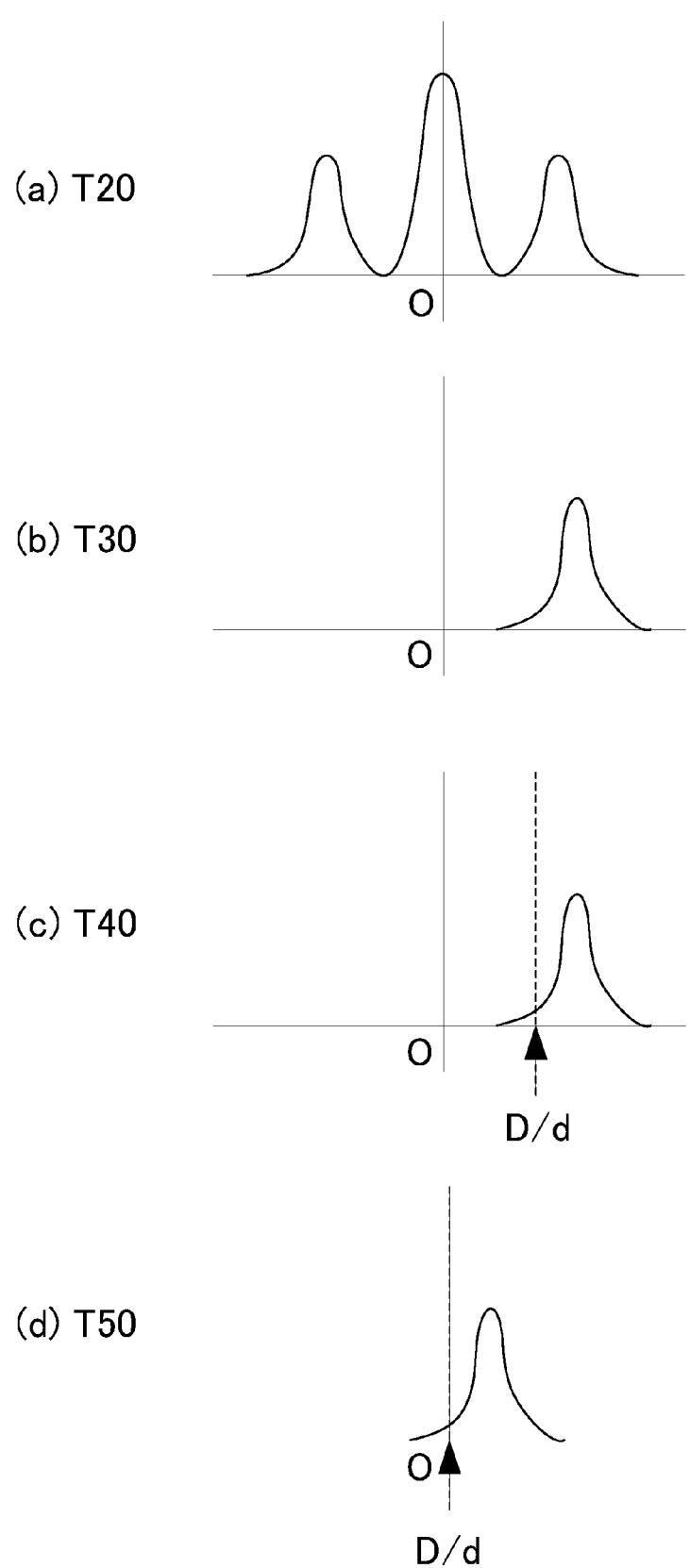
FIG. 3 is a schematic diagram of signal waveforms in each step of FIG. 2.

FIG. 2 is a flow diagram of the transmitted wavefront measuring method in the present embodiment. In FIG. 2, a flow diagram of obtaining a transmitted wavefront including a focus component is shown. FIG. 3 is a schematic diagram of signal waveforms in each step of FIG. 2. However, the signal waveforms shown in FIG. 3 are different from real signal waveforms in the number of the signals or the like. Hereinafter, referring to FIGS. 2 and 3, the transmitted wavefront measuring method in the present embodiment will be described.

First, in Step T10, a controller 160 of the transmitted wavefront measuring apparatus obtains an interference pattern formed on the CCD 140. Specifically, the laser light 101 is emitted from the laser light source 100 onto the test object 120, and the interfering light which has transmitted through the test object 120 and also the diffraction grating 130 disposed behind the test object 120 is received by the CCD 140 disposed at a predetermined distance behind the diffraction grating 130. The predetermined distance is equal or similar to a Talbot distance. The controller 160 measures an intensity distribution of the interfering light received by the CCD 140.

Subsequently, in Step T20, the controller 160 performs an FFT (Fast Fourier Transform) processing for the obtained interference pattern to calculate a frequency map. In other words, a frequency distribution calculator of the controller 160 performs a Fourier transform of the intensity distribution of the interfering light to calculate a frequency distribution (a frequency spectrum). FIG. 3A shows a signal waveform of the frequency spectrum obtained in Step T20. Next, in Step T30, the controller 160 cuts out a primary frequency spectrum that is an interference component between lights which have diffraction orders of the diffracted lights displaced by one from each other. FIG. 3B shows a signal waveform of the primary frequency spectrum obtained in Step T30. Further, in Step T40, the controller 160 calculates a frequency $f_g$ (grating frequency) represented by the following expression (4) using a grating period d of the diffraction grating 130 and a light receiving surface size D of the CCD 140 (FIG. 3C).

$$f_g = \frac{D}{d} \quad (4)$$

Next, in Step T50, the controller 160 moves the primary frequency spectrum cut out and extracted in Step T30 so that the frequency $f_g$ (the grating frequency) is coincident with an original point O. This is performed because a difference between the primary frequency spectrum and the frequency $f_g$ corresponds to a focus component. FIG. 3D shows a signal waveform of the primary frequency spectrum moved in Step T50. A formula manipulation on the frequency map is completed by the above flow diagram (Steps T10 to T50).

Subsequently, in Step T60, the controller 160 performs an iFFT (inverse Fast Fourier Transform) processing for the frequency map obtained by the above flow diagram to calculate a complex amplitude of a difference of wavefronts of the diffracted lights. Then, in Step T70, the controller 160 calculates a phase term of the obtained complex amplitude. Further, the controller 160 performs a difference Zernike fitting in Step T80, and performs a fitting of the wavefront shape of the transmitted wavefront to calculate the transmitted wavefront including the focus component in Step T90.

The above Steps T30 to T90 are steps of obtaining a transmitted wavefront of the test object 120 based on a primary frequency spectrum in a frequency distribution, and are performed by a transmitted wavefront calculator of the controller 160. The steps include steps (Steps T50 and T60) which perform an inverse Fourier transform of the primary frequency spectrum on the basis of the frequency $f_g$ (the grating frequency) of the diffraction grating 130 to calculate a complex amplitude of the interfering light. Further, the steps include steps (Steps T70 to T90) which obtain the transmitted wavefront of the test object 120 based on the complex amplitude of the interfering light. According to the transmitted wavefront measuring method of the present embodiment, a transmitted wavefront with a large aberration including the focus component can be measured with high accuracy by following the above flow diagram.

The difference Zernike fitting performed in Step T80 is a fitting method of obtaining a coefficient of a Zernike polynomial which represents the difference of the wavefront most appropriately. In the present embodiment, Step T80 is not limited to the difference Zernike fitting method, but another method can also be used if it is a wavefront recovering method such as an integral method which is commonly used by a shearing interferometer.

In the present embodiment, a transmitted wavefront with a large aberration can be measured by using a Talbot interferometer as a transmitted wavefront measuring apparatus. The Talbot interferometer is a kind of lateral shearing interferometer, and is configured to measure, as an interference pattern, a difference with respect to its own transmitted wavefront which has been laterally displaced (sheared). Thus, the shearing interferometer is a measuring apparatus which obtains an amount corresponding to a tilt of the transmitted wavefront. The lateral displacement amount of the transmitted wavefront is called an shear amount, and is also capable of performing a measurement, as a small aberration to the extent that the interference pattern is not thickened (a shear wavefront), with respect to a large aberration of the transmitted wavefront by reducing the shear amount.

Commonly, the accuracy of a shearing interferometer is deteriorated because a shear wavefront is buried in a noise when the shear amount is too small. Therefore, it is preferable that the shear amount is around 3 to 5% with respect to a diameter of a pupil. In the present embodiment, however, since the transmitted wavefront having a large aberration is measured using the shear wavefront having a small aberration, the shear amount is decreased to equal to or less than 1.5% and preferably decreased up to around 0.3 to 0.9%. The shear amount SHEAR is defined by the following expression (5) using a distance $Z_t$ between the diffraction grating 130 and the CCD 140 and a diameter $D_i$ of interference pattern data on the CCD 140.

$$\text{shear} = \frac{\lambda Z_t}{d D_i} \quad (5)$$

Expression (5) is represented as the following expression (6) using Expression (1) and a diameter $D_0$ of a light beam on the diffraction grating 130.

$$\text{shear} = \frac{2Nd}{D_0} \quad (6)$$

It is found that the shear amount SHEAR and a pitch d (period) of the diffraction grating 130 are proportional in view of the above Expression (6). As represented by Expression (1), because the pitch d of the diffraction grating 130 also influences on the distance $Z_t$ between the diffraction grating 130 and the CCD 140, it needs to be determined by considering the interference between each element. For example, when 2N (2N is an integer) is equal to 1 on condition that the diameter $D_0$ of the light beam on the diffraction grating 130 is around 10 to 20 mm, it is preferable that the pitch d of the diffraction grating 130 is around 40 to 180 µm.

Embodiment 2

Figure 4:
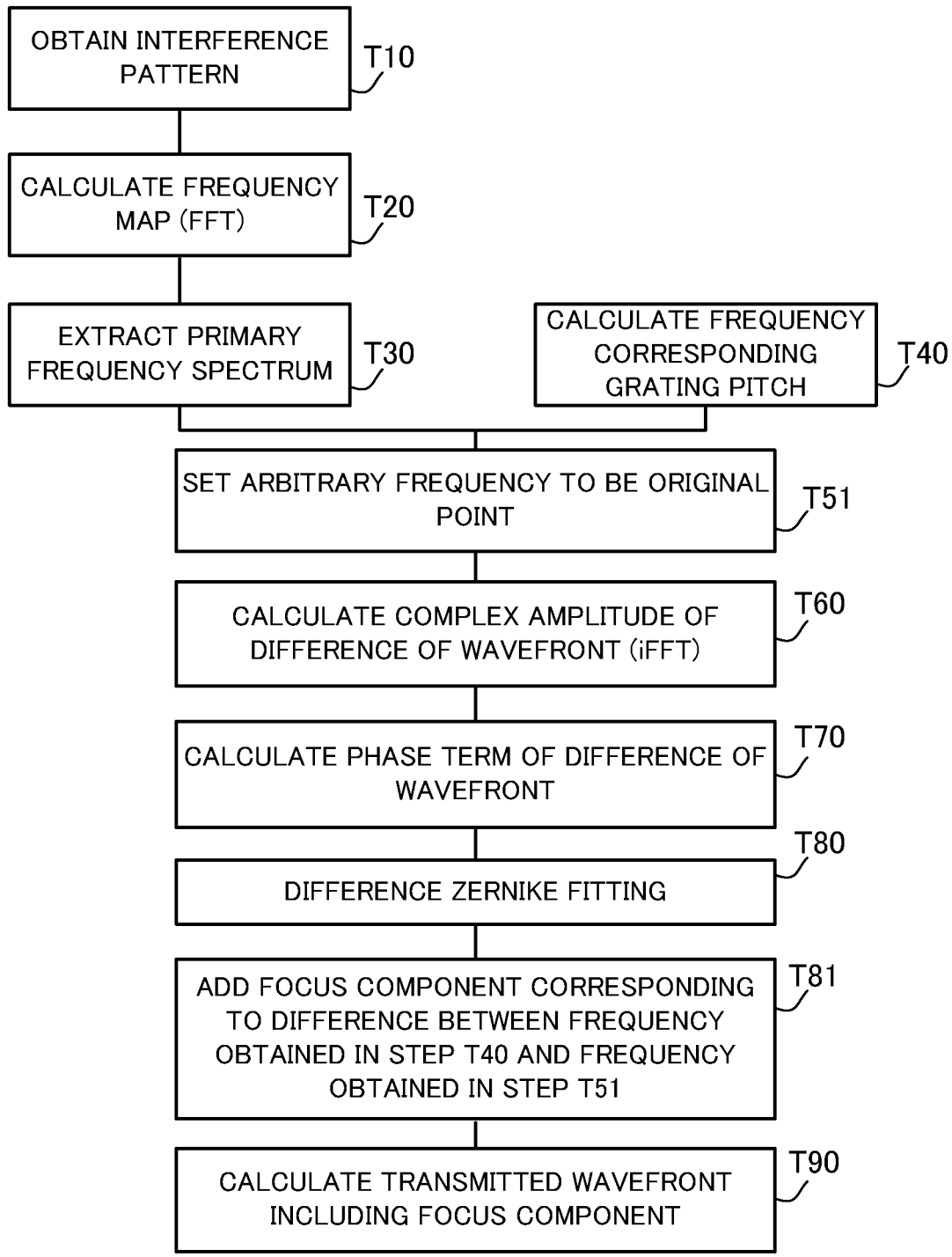
FIG. 4 is a flow diagram of a second transmitted wavefront measuring method (Embodiment 2).

Next, a transmitted wavefront measuring method in Embodiment 2 of the present invention will be described. FIG. 4 is a flow diagram of the transmitted wavefront measuring method in the present embodiment. As shown in FIG. 4, a basic flow diagram of the transmitted wavefront measuring method of the present embodiment is the same as that of FIG. 2. However, the present embodiment is different from Embodiment 1 in that Step T51 instead of Step T50 is inserted and also Step T81 is inserted between Steps T80 and T90.

On a frequency map, performing Step T50 of Embodiment 1 may be difficult. In such a case, a controller 160 sets an arbitrary frequency of a primary frequency spectrum as an original point in Step T51 instead of Step T50. Further, in Step T81 after Step T80, the controller 160 adds a focus component which corresponds to a difference between a frequency $f_g$ (a grating frequency) obtained in Step T40 and an arbitrary frequency obtained in Step T51 to original spectrum information. In other words, the controller 160 calculates the focus component based on the difference between the primary frequency spectrum and the frequency $f_g$ to obtain the transmitted wavefront of a test object 120. According to the transmitted wavefront measuring method of the present embodiment, the transmitted wavefront of the test object including the focus component can be calculated with high accuracy.

Embodiment 3

Next, a refractive-index distribution measuring method in Embodiment 3 of the present invention will be described. The refractive-index distribution measuring method of the present embodiment is a measuring method of measuring a refractive-index distribution inside a single lens (a test object) including a focus component with high accuracy.

Figure 5A:
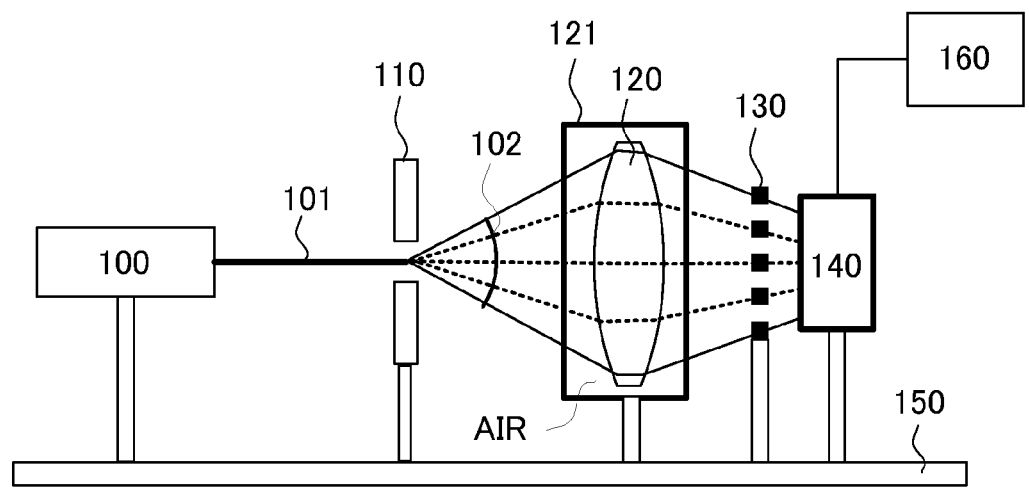
FIGS. 5A and 5B are schematic configuration diagrams of a second transmitted wavefront measuring apparatus (Embodiment 3).
Figure 5B:
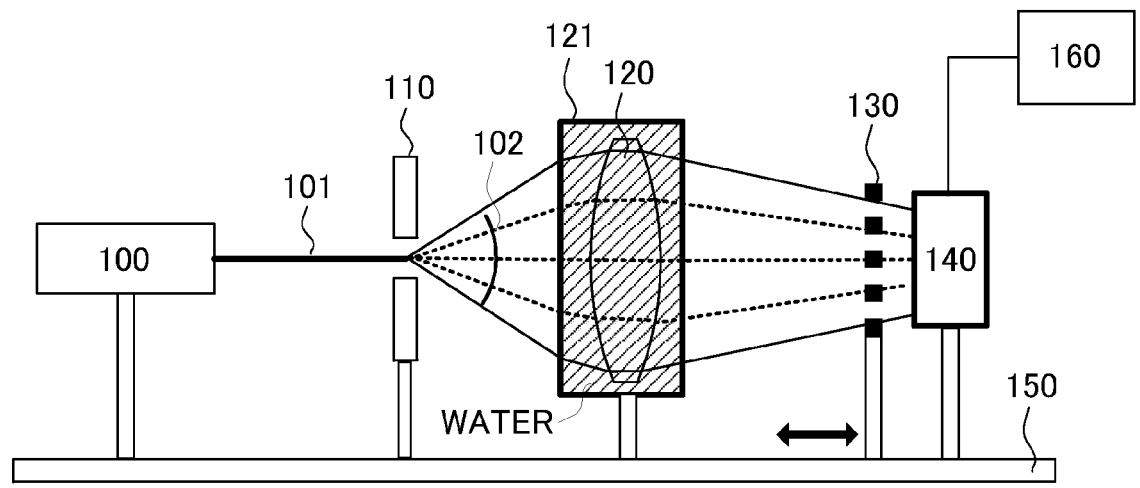

FIGS. 5A and 5B are schematic configuration diagrams of a transmitted wavefront measuring apparatus (a Talbot interferometer) in the present embodiment. FIG. 5A shows a state where the test object is measured in the air (in a first medium), and FIG. 5B shows a state where the test object is measured in water (in a second medium). Since the basic configurations shown in FIGS. 5A and 5B are the same as that of the Talbot interferometer of FIG. 1, the description in the present embodiment will be focused on parts different from that of the Talbot interferometer of FIG. 1.

The Talbot interferometer of the present embodiment includes a test object case 121 for holding a test object 120, and the test object 120 is installed in the test object case 121. The test object case 121 is configured to be filled with a medium such as air or water to immerse the test object 120 in the medium. Laser light 102 that has passed through the test object 120 and the test object case 121 is received by the CCD 140 via the diffraction grating 130. Similarly to the laser light source 100 or the like, the test object case 121 is disposed on the rail 150 which is arranged in parallel to the optical axis of the test object 120, and is configured to be movable on the rail 150. As shown in FIG. 5B, when the waver is introduced in the test object case 121, the diffraction grating 130 and the CCD 140 are arranged at a distance from the test object 120 as compared with the case where the air is introduced in the test object case 121 (FIG. 5A).

Figure 6:
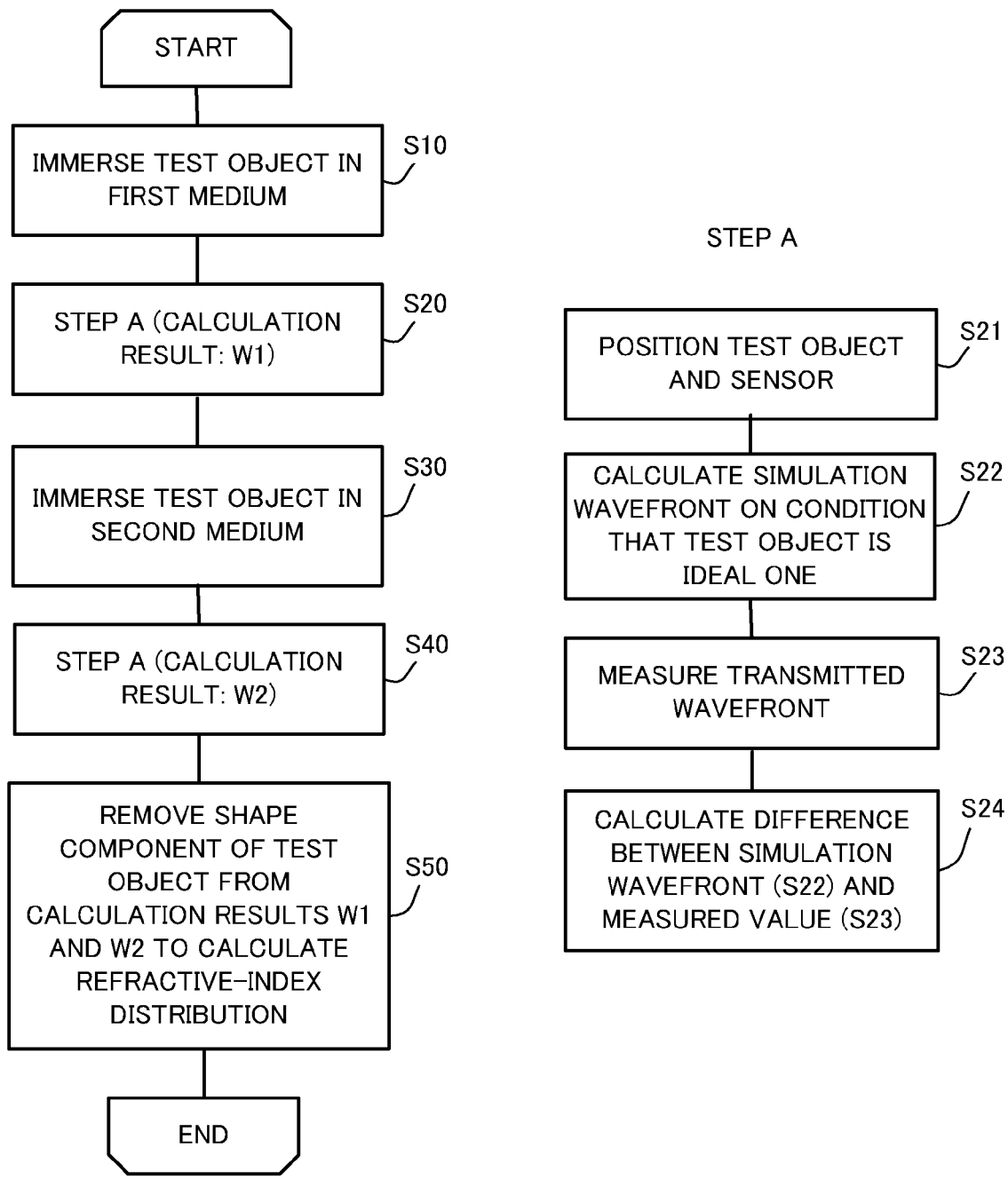
FIG. 6 is a flow diagram of a refractive-index distribution measuring method utilizing the apparatus of FIGS. 5A and 5B.

Next, a refractive-index distribution measuring method using the transmitted wavefront measuring apparatus in the present embodiment will be described. FIG. 6 is a flow diagram showing a calculation procedure of a refractive-index distribution $W_{index}$ of the test object (a refractive-index distribution measuring method). As shown in FIG. 5A, first, in Step S10, the air (the first medium) is introduced in the test object case 121 and the test object 120 is installed. The test object 120 is immersed in the air inside the test object case 121. Subsequently, in Step S20, the controller 160 calculates a wavefront aberration W1 in a state where the air is introduced inside the test object case 121. The wavefront aberration W1 is calculated in accordance with a flow diagram of Step A shown at the right side of FIG. 6. Specifically, Step A of calculating the wavefront aberration W1 includes the following four steps.

First, in Step S21, the controller 160 moves the test object 120 and a sensor constituted by the diffraction grating 130 and the CCD 140 on the rail 150 to dispose them at optimal positions. Next, in Step S22, the controller 160 calculates a simulation wavefront $W_{sim}$, on condition that the test object 120 is ideal one. Step S22 is a step of calculating a transmitted wavefront on condition that the test object 120 and the sensor are disposed at the same positions as those in Step S21 and a refractive index of the test object 120 is uniform.

Subsequently, in Step S23, the controller 160 actually measures a transmitted wavefront $W_m$ using the transmitted wavefront measuring apparatus (for example, the Talbot interferometer shown in FIGS. 5A and 5B). Step S23 corresponds to a transmitted wavefront restoring step (Steps T10 to T90) of the flow diagram shown in FIG. 2. Next, in Step S24, the controller 160 obtains a difference W1 between the simulation wavefront $W_{sim}$ obtained in Step S22 and the transmitted wavefront $W_m$ obtained in Step S23. As above, Step A is completed.

Next, in Step S30, water is introduced in the test object case 121 and the test object 120 is installed (FIG. 5B). The test object 120 is immersed in the water inside the test object case 121. In Step S40, the controller 160 calculates a wavefront aberration W2 on condition that the test object 120 is immersed in the water in accordance with the procedure of Step A described above. Subsequently, in Step S50, the controller 160 removes a shape component of the test object 120 from the wavefront aberrations W1 and W2 using the following expression (7) to calculate a refractive-index distribution $W_{index}$ of the test object 120.

$$W_{index} = \frac{(Ng - N_1)W2 - (Ng - N_2)W1}{N_2 - N_1} \quad (7)$$

In the expression (7), Ng is a design value of a refractive index of a glass, N1 is a refractive index of air, and N2 is a refractive index of water.

Thus, in the present embodiment, a step of measuring a first transmitted wavefront of the test object 120 in the first medium whose refractive index is different from that of the test object 120 (Step S20) is included. A step of measuring a second transmitted wavefront of the test object 120 in the second medium whose refractive index is different from those of the test object 120 and the first medium (Step S40) is also included. Further, a step of calculating the refractive-index distribution $W_{index}$ of the test object 120 based on the first transmitted wavefront and the second transmitted wavefront (Step S50) is included. The steps of measuring the first transmitted wavefront and the second transmitted wavefront are for example measured by using the transmitted wavefront measuring method of Embodiment 1 or 2. As above, a calculation flow of the refractive-index distribution is completed. According to the refractive-index distribution measuring method of the present embodiment, the refractive-index distribution of the test object can be measured including the focus component with high accuracy.

In the present embodiment, the air and the water are used as a first medium and a second medium, respectively, but the present embodiment is not limited to them. If they are two kinds of media which have refractive indexes different by at least around 0.01 from each other, a combination other than the combination of the air and the water may also be applied. Further, as two kinds of media, the same materials whose temperatures are different to change refractive indexes can also be used. In addition, when the refractive-index distribution is roughly measured, Steps S22 and S24 may also be omitted to use the transmitted wavefront measuring value as the wavefront aberrations W1 and W2 in Step A.

The transmitted wavefront measuring method and the refractive-index measuring method of each of the above embodiments can be used for a manufacturing method of an optical element such as a lens. In this case, the optical performance of the optical element is evaluated to fabricate the optical element based on the transmitted wavefront or the refractive-index distribution (measurement result) of the optical element measured by the transmitted wavefront measuring method or the refractive-index measuring method. The optical element is manufactured by passing through a step of correcting an optical surface after the optical performance has been evaluated. According to such a manufacturing method, an optical element with high optical performance can be mass-produced even if it is manufactured by using a mold or the like.

The embodiments of the present invention have described the case where light transmitted through an object to be measured enters the diffraction grating, but the disposed positions of the object to be measured and the diffraction grating can be replaced. In other words, in the present invention, the diffraction grating and the object to be measured can also be disposed so that the light transmitted through the diffraction grating enters the object to be measured.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2009-074273, filed on Mar. 25, 2009, which is hereby incorporated by reference herein in its entirety.

What is claimed is:

1. A transmitted wavefront measuring method comprising the steps of:
 emitting light from a light source onto an object to be measured to receive interfering light transmitted through the object to be measured and a diffraction grating on a light receiving portion disposed at a predetermined distance from the diffraction grating to measure an intensity distribution of the interfering light;
 performing a Fourier transform of the intensity distribution of the interfering light to calculate a frequency distribution; and
 obtaining a transmitted wavefront of the object to be measured based on a primary frequency spectrum in the frequency distribution,
 wherein the step of obtaining the transmitted wavefront comprises the steps of:
  performing an inverse Fourier transform of the primary frequency spectrum with reference to a grating frequency of the diffraction grating to calculate a complex amplitude of the interfering light, and
  obtaining the transmitted wavefront, including a focus component, corresponding to a difference between the primary frequency spectrum and the grating frequency.

2. A method of manufacturing an optical element comprising the steps of:
 measuring a transmitted wavefront of the optical element by:
  emitting light from a light source onto the optical element to receive interfering light transmitted through the optical element and a diffraction grating on a light receiving portion disposed at a predetermined distance from the diffraction grating to measure an intensity distribution of the interfering light;
  performing a Fourier transform of the intensity distribution of the interfering light to calculate a frequency distribution; and
  obtaining a transmitted wavefront of the optical element based on a primary frequency spectrum in the frequency distribution,
  wherein the step of obtaining the transmitted wavefront comprises the steps of:
   performing an inverse Fourier transform of the primary frequency spectrum with reference to a grating frequency of the diffraction grating to calculate a complex amplitude of the interfering light, and
   obtaining the transmitted wavefront including a focus component, corresponding to a difference between the primary frequency spectrum and the grating frequency; and
 correcting an optical surface of the optical element based on the transmitted wavefront of the optical element measured in the step of measuring the transmitted wavefront of the optical element.

3. A method of manufacturing an optical element comprising the steps of:
 measuring a refractive-index distribution of the optical element by:
  measuring a first transmitted wavefront of the optical element in a first medium whose refractive index is different from that of the optical element;
  measuring a second transmitted wavefront of the optical element in a second medium whose refractive index is different from the optical element and the first medium; and
  calculating a refractive-index distribution of the object to be measured based on the first transmitted wavefront and the second transmitted wavefront,
  wherein the steps of measuring the first transmitted wavefront and the second transmitted wavefront each comprise the steps of:
   emitting light from a light source onto the optical element to receive interfering light transmitted through the optical element and a diffraction grating on a light receiving portion disposed at a predetermined distance from the diffraction grating to measure an intensity distribution of the interfering light;
   performing a Fourier transform of the intensity distribution of the interfering light to calculate a frequency distribution; and
   obtaining a transmitted wavefront of the optical element based on a primary frequency spectrum in the frequency distribution by:
    performing an inverse Fourier transform of the primary frequency spectrum with reference to a grating frequency of the diffraction grating to calculate a complex amplitude of the interfering light, and
    obtaining the transmitted wavefront of the optical element based on the complex amplitude of the interfering light; and
 correcting the optical surface of the optical element based on the refractive index distribution of the optical element measured in the step of measuring the refractive index distribution.

4. A transmitted wavefront measuring apparatus comprising:
 a light source configured to emit light onto an object to be measured;
 a diffraction grating configured so that the light emitted from the light source enters the diffraction grating;
 a light receiving portion configured to be disposed at a predetermined distance from the diffraction grating and to receive an intensity distribution of an interfering light transmitted through the object to be measured and the diffraction grating; and
 a controller programmed to provide:
  a frequency distribution calculation task that performs a Fourier transform of the intensity distribution of the interfering light to calculate a frequency distribution; and
  a transmitted wavefront calculation task that obtains a transmitted wavefront of the object to be measured based on a primary frequency spectrum in the frequency distribution by:

performing an inverse Fourier transform of the primary frequency spectrum with reference to a grating frequency of the diffraction grating to calculate a complex amplitude of the interfering light, and obtaining the transmitted wavefront, including a focus component, corresponding to a difference between the primary frequency spectrum and the grating frequency.

5. A refractive-index distribution measuring method comprising the steps of:

measuring a first transmitted wavefront of an object to be measured in a first medium whose refractive index is different from that of the object to be measured;

measuring a second transmitted wavefront of the object to be measured in a second medium whose refractive index is different from the object to be measured and the first medium; and calculating a refractive-index distribution of the object to be measured based on the first transmitted wavefront and the second transmitted wavefront, wherein the steps of measuring the first transmitted wavefront and the second transmitted wavefront each comprise the steps of:

emitting light from a light source onto the object to be measured to receive interfering light transmitted through the object to be measured and a diffraction grating on a light receiving portion disposed at a predetermined distance from the diffraction grating to measure an intensity distribution of the interfering light;

performing a Fourier transform of the intensity distribution of the interfering light to calculate a frequency distribution; and obtaining a transmitted wavefront of the object to be measured based on a primary frequency spectrum in the frequency distribution by:

performing an inverse Fourier transform of the primary frequency spectrum with reference to a grating frequency of the diffraction grating to calculate a complex amplitude of the interfering light, and obtaining the transmitted wavefront of the object to be measured based on the complex amplitude of the interfering light.

* * * * *